US00PP26201P2

(12) United States Plant Patent
de Groot

(10) Patent No.: US PP26,201 P2
(45) Date of Patent: Dec. 8, 2015

(54) *HYPERICUM* PLANT NAMED 'RUIHYH004B'

(50) Latin Name: *Hypericum×inodorum*
Varietal Denomination: Ruihyh004b

(71) Applicant: Henk C. A. de Groot, Amstelveen (NL)

(72) Inventor: Henk C. A. de Groot, Amstelveen (NL)

( * ) Notice: Subject to any disclaimer, the term of this patent is extended or adjusted under 35 U.S.C. 154(b) by 108 days.

(21) Appl. No.: 13/998,748

(22) Filed: Dec. 3, 2013

(51) Int. Cl.
*A01H 5/02* (2006.01)

(52) U.S. Cl.
USPC ..... Plt./442

(58) Field of Classification Search
USPC ..... Plt./442, 263.1, 226
CPC ..... A01H 5/02; A01H 5/00
See application file for complete search history.

(56) References Cited

PUBLICATIONS http://www.eshraghinursery.com/material.html?0=2560760&1=Hypericum+hybrida+Kiwi+Hypearl+Harvest+Festival%E2%84%A2+Green+PPAF 2 pages, 2009.*

* cited by examiner

*Primary Examiner* — Kent L Bell
(74) *Attorney, Agent, or Firm* — Penny J. Aguirre

(57) ABSTRACT

A new cultivar of *Hypericum×inodorum*, 'Ruihyh004b', characterized by its compact plant habit suitable for container growing, its medium sized berries that are green in color and ovate in shape, and its medium to small sized light green sepals that are ovate in shape.

2 Drawing Sheets

Botanical classification: *Hypericum×inodorum.*
Variety denomination: 'Ruihyh004b'.

BACKGROUND OF THE INVENTION

The present invention relates to a new and distinct cultivar of *Hypericum×inodorum* and will be referred to hereafter by its cultivar name, 'Ruihyh004b'. 'Ruihyh004b' is a semi-evergreen shrub grown for use as a landscape plant and container plantings.

The new cultivar was derived from a controlled breeding program conducted by the Inventor in Hazerswoude, The Netherlands. The overall purpose of the breeding program was to develop new cultivars of *Hypericum* plants with unique berries and improved resistance to *Melampsora hypericorum.*

The new cultivar arose from a cross made by the Inventor in Hazerswoude, The Netherlands in April 2007 between an unnamed plant from the Inventor's breeding program, designated 'Ruihyd064A' as the female parent and 'Jolly Hypearl' (not patented) as the male parent. The Inventor selected 'Ruihyh004b' as a single unique plant amongst the seedlings that resulted from the above cross in autumn of 2008.

Asexual propagation of the new cultivar was first accomplished by the Inventor by vegetative stem cuttings in 2010 in Hazerswoude, The Netherlands. Asexual propagation by vegetative stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Ruihyh004b' as a unique cultivar of *Hypericum.*

1. 'Ruihyh004b' exhibits a compact plant habit suitable for container growing.
2. 'Ruihyh004b' exhibits medium sized berries that are green in color and ovate in shape.
3. 'Ruihyh004b' exhibits medium to small sized light green sepals that are ovate in shape.

The female parent of 'Ruihyh004b', 'Ruihyd064a', differs from 'Ruihyh004b' in having berries that are light pink in color. The male parent of 'Ruihyh004b', 'Jolly Hypearl', differs from 'Ruihyh004b' in having berries that are red in color. 'Ruihyh004b' can be most closely compared to the cultivar 'Green Hypearl' (not patented). 'Green Hypearl' differs from 'Ruihyh004b' in having berries that are slightly darker in color with a brown tint and in having berries that are long ovate in shape. 'Ruihyh004b' can also be compared to its sibling cultivar 'Ruihyh004c' (U.S. Plant patent application Ser. No. 13/998,749). 'Ruihyh004c' is similar to 'Ruihyh004b' in having a compact plant habit. 'Ruihyh004c' differs from 'Ruihyh004b' in having berries that are creamy white in color, in having sepals that are larger in size, and in having stamens that are held in a more open, horizontal position.

BRIEF DESCRIPTION OF THE DRAWINGS

The accompanying colored photographs illustrate the overall appearance and distinct characteristics of the new *Hypericum*. The plants in the photographs were taken of plants two years in age as grown in a one-gallon container in a greenhouse in Lelystad, The Netherlands.

The photograph in FIG. 1 provides a side view of 'Ruihyh004b' in bloom.

Figure 1:
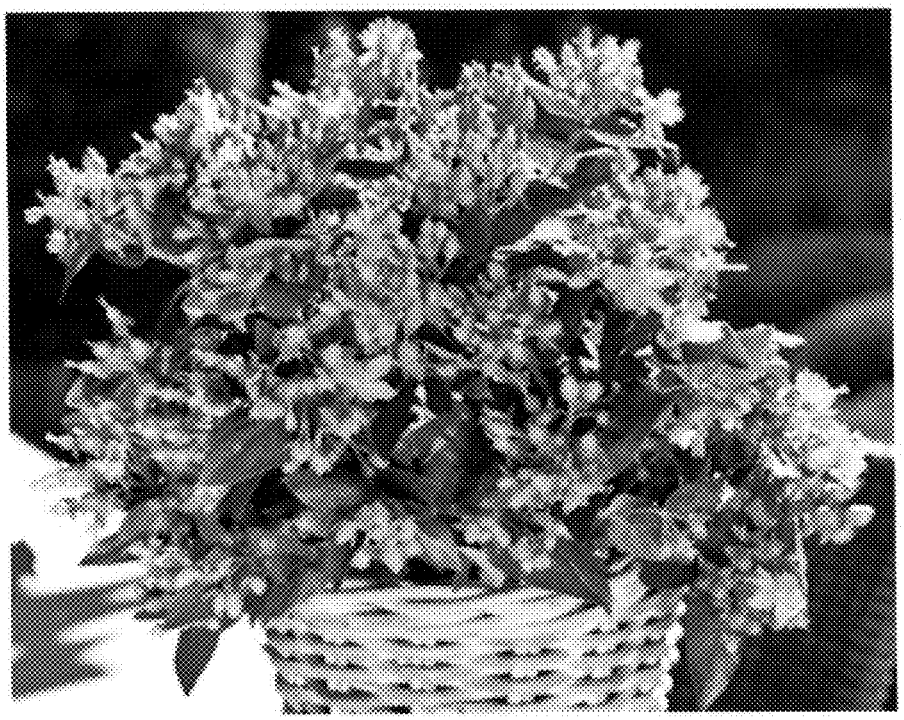
Figure 2:
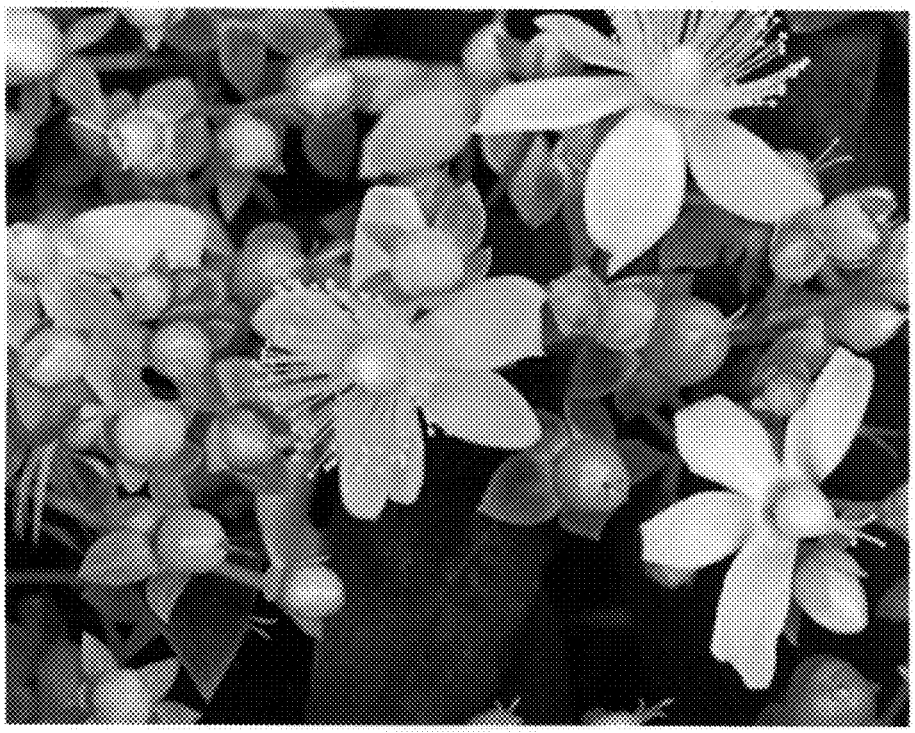

The photograph in FIG. 2 provides a close-up view of flowers and berries of 'Ruihyh004b'.

The colors in the photographs are as close as possible with the digital photography techniques available and the color values cited in the detailed botanical description accurately describe the colors of the new *Hypericum*.

DETAILED BOTANICAL DESCRIPTION

The following is a detailed description of two year-old plants of the new cultivar as grown outdoors in 2-gallon containers in Davidsonville, Md. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—From July to September in The Netherlands.

*Plant type*.—Semi-evergreen shrub.

*Plant habit*.—Compact with suitability for container growing.

*Height and spread*.—Reaches an average of 35 cm in height and 40 cm in width.

*Cold hardiness*.—Observed to be hardy to at least −10° C.

*Diseases*.—Has shown tolerance to *Melampsora hypericorum*.

*Root description*.—Fibrous and fine.

*Propagation*.—Vegetative stem cuttings.

*Growth rate*.—Moderate, typical for cultivars of *Hypericum×inodorum*.

Stem description:

*Shape*.—Round.

*Stem color*.—New growth, 144C, maturing branches become 165A as they become woody.

*Stem size*.—Main stems; 34 cm in length and 4 mm in width, lateral branches; an average of 30 cm in length and 1.5 mm in width.

*Stem surface*.—Glabrous.

*Internode length*.—Average of 1.4 cm.

*Branching*.—Freely branched with lateral branches cascading.

Foliage description:

*Leaf shape*.—Elliptic.

*Leaf division*.—Simple.

*Leaf base*.—Cuneate.

*Leaf apex*.—Acute.

*Leaf fragrance*.—None.

*Leaf venation*.—Pinnate, not conspicuous, 144D on upper surface, 139D on lower surface.

*Leaf margins*.—Entire.

*Leaf arrangement*.—Opposite, aspect is horizontal.

*Leaf attachment*.—Sessile.

*Leaf surface*.—Glabrous on upper surface, finely puberulent on lower surface.

*Leaf size*.—Up to about 3.5 cm in length, up to about 1.8 cm in width.

*Leaf color*.—Newly expanded leaves; upper surface a color between 144B and 144C, lower surface a color between 144C and 144D, mature leaves; upper surface N137A, lower surface 138B.

Inflorescence description:

*Inflorescence type*.—Solitary flowers from terminal of lateral branches.

*Flower buds*.—Conical in shape with acute apex, up to 8 mm in length and 5 mm in width prior to opening, calyx portion is wrapped around petals, petal portion 21A in color.

*Flower fragrance*.—None detected.

*Flower quantity*.—About 7 per lateral branch.

*Flower type*.—Complete, rotate with reflexed to horizontal petals and prominent stamens and ovary.

*Flower aspect*.—Upward facing.

*Flower lastingness*.—About 5 days.

*Flower size*.—Average of 2 cm in diameter and depth.

*Petals*.—5, oblong in shape, un-fused, curved inward and becoming horizontal, upper surface is glabrous and lower surface is satiny, entire margin, rounded base, rounded apex with single slight notched, about 1 cm in length and 6 mm in width, color is 13A (opening and mature, lower and upper surface).

*Calyx*.—Reflexed, un-fused sepals, about 5 mm in diameter and 3 mm in depth.

*Sepals*.—5, lanceolate in shape, 138A in color on upper surface and 138B in color on lower surface, glabrous on upper and lower surface, up to 6 mm in length and 3 mm in width, entire margin, round-truncate base, acute-attenuate apex.

*Peduncles*.—About 1.5 cm in length, 1 mm in width, 144B in color, glabrous surface.

*Pedicels*.—About 8 mm in length, 1.5 mm in width, 145B in color, glabrous surface.

Reproductive organs:

*Gynoecium*.—Compound pistil about 1.5 cm in length and 4 mm in width, styles; 34A in color and about 8 mm in length and 0.5 mm in length, stigmas; 3, 187A in color about 1 mm in diameter, ovary is superior and 144A in color, about 6 mm in length and 4 mm in width.

*Androecium*.—Numerous stamens (about 100, arranged in 5 tufts), spreading outward from base of ovary extending about 1 cm in diameter, filaments are 17B in color, about 8 mm in length and 0.4 mm in width, anthers are 147D in color, dorsifixed, about 2 mm in length and width, pollen was not visible.

*Fruit*.—Ovate in shape with a rounded apex, glabrous and satiny surface, and average of 6 mm in length and 4 mm in width, matures to a blend of 144A and 144B in color.

It is claimed:

1. A new and distinct cultivar of *Hypericum* plant named 'Ruihyh004b' as herein illustrated and described.

* * * * *